US008415142B2

(12) United States Patent
Kertz

(10) Patent No.: US 8,415,142 B2
(45) Date of Patent: *Apr. 9, 2013

(54) METHOD AND APPARATUS FOR CO₂ SEQUESTRATION

(76) Inventor: Malcolm Glen Kertz, El Paso, TX (US)

( * ) Notice: Subject to any disclaimer, the term of this patent is extended or adjusted under 35 U.S.C. 154(b) by 1207 days.

This patent is subject to a terminal disclaimer.

(21) Appl. No.: 12/128,294

(22) Filed: May 28, 2008

(65) Prior Publication Data

US 2008/0274494 A1 Nov. 6, 2008

Related U.S. Application Data

(63) Continuation-in-part of application No. 11/762,295, filed on Jun. 13, 2007.

(60) Provisional application No. 60/892,331, filed on Mar. 1, 2007, provisional application No. 60/804,763, filed on Jun. 14, 2006.

(51) Int. Cl.
| | |
|---|---|
| *A01G 7/00* | (2006.01) |
| *A01H 13/00* | (2006.01) |
| *C12M 1/36* | (2006.01) |
| *C12M 1/38* | (2006.01) |
| *C12M 1/12* | (2006.01) |
| *C12M 1/09* | (2006.01) |
| *C12M 1/00* | (2006.01) |
| *C12M 3/00* | (2006.01) |
| *C12M 1/24* | (2006.01) |

(52) U.S. Cl. ......... 435/292.1; 47/1.4; 47/17; 435/257.1; 435/286.6; 435/286.7; 435/296.1; 435/304.1

(58) Field of Classification Search .... 435/283.1–309.4; 47/1.4, 17

See application file for complete search history.

(56) References Cited

U.S. PATENT DOCUMENTS

| | | | | |
|---|---|---|---|---|
| 1,798,565 | A | * 3/1931 | Trullinger | ...... 248/129 |
| 2,312,221 | A | * 2/1943 | Powell et al. | ...... 210/755 |
| 3,224,143 | A | * 12/1965 | Tew et al. | ...... 435/168 |
| 4,831,196 | A | 5/1989 | Buonicore et al. | |

(Continued)

FOREIGN PATENT DOCUMENTS

| | | |
|---|---|---|
| CN | 1089991 A | 7/1994 |
| CN | 1201827 A | 12/1998 |

(Continued)

OTHER PUBLICATIONS

PCT International Search Report and Written Opinion for Appl. No. PCT/US2007/071165 dated Dec. 14, 2007; (pp. 7).

(Continued)

*Primary Examiner* — Nathan Bowers
*Assistant Examiner* — Lydia Edwards
(74) *Attorney, Agent, or Firm* — Conley Rose, P.C.

(57) ABSTRACT

A method and apparatus for growing algae for sequestering carbon dioxide and then harvesting the algae includes a container for a suspension of algae in a liquid and a bioreactor having a translucent channel in fluid communication with the container to absorb CO₂ and grow the algae. A monitor determines the growth of the algae in the channel. A separator separates the grown algae from the suspension and an extractor extracts biomaterials from the grown algae.

38 Claims, 11 Drawing Sheets

U.S. PATENT DOCUMENTS

| | | | |
|---|---|---|---|
| 4,970,166 A | | 11/1990 | Mori |
| 5,454,625 A * | | 10/1995 | Christensen et al. ............ 298/18 |
| 5,476,787 A | | 12/1995 | Yokoyama et al. |
| 5,506,117 A * | | 4/1996 | Andrews et al. ................. 435/29 |
| 5,534,417 A * | | 7/1996 | Arad et al. ...................... 435/67 |
| 5,614,378 A | | 3/1997 | Yang et al. |
| 5,707,868 A | | 1/1998 | Boulay et al. |
| 5,981,271 A | | 11/1999 | Doucha et al. |
| 6,509,188 B1 | | 1/2003 | Trosch et al. |
| 6,571,735 B1 | | 6/2003 | Wilkinson |
| 6,667,171 B2 | | 12/2003 | Bayless et al. |
| 2005/0260553 A1* | | 11/2005 | Berzin ............................. 435/3 |
| 2007/0048848 A1 | | 3/2007 | Sears |
| 2007/0048859 A1 | | 3/2007 | Sears |
| 2008/0086938 A1 | | 4/2008 | Hazlebeck et al. |
| 2008/0087165 A1 | | 4/2008 | Wright et al. |

FOREIGN PATENT DOCUMENTS

| | | |
|---|---|---|
| DE | 20017229 | 3/2002 |
| EP | 0576870 A2 | 1/1994 |
| EP | 0935991 A1 | 8/1999 |
| GB | 2235210 | 2/1991 |
| JP | 5236935 A | 9/1993 |
| WO | 2005121309 A1 | 12/2005 |
| WO | 2007098150 | 8/2007 |
| WO | 2007147028 | 12/2007 |

OTHER PUBLICATIONS

International Search Report and Written Opinion dated May 31, 2010 for Appl. PCT/US2009/045421; (5 p.).

GCC/P/2007/8509 Examination Report and Novelty Search dated Mar. 19, 2009 (9 p.).

GCC/P/2007/8509 Examination Report dated Mar. 3, 2010 (5 p.).

Malaysian Examination Report dated Mar. 31, 2011; Malaysian Application No. PI 20070930 (3 p.).

Malaysian Response to Examination Report dated Mar. 31, 2011; Malaysian Application No. PI 20070930; Response filed Aug. 10, 2011 (6 p.).

Panama Examination Report dated Jun. 5, 2008; Panamanian Application No. 87311 (3 p.).

Panama Response to Examination Report dated Jun. 5, 2008; Response filed Mar. 23, 2009; Panamanian Application No. 87311 (7 p.).

Chinese 2nd Office Action Dated Aug. 2, 2012; Chinese Application No. 200780022235.9 (12 p.).

Office Action Dated May 25, 2011; U.S. Appl. No. 11/762,295 (13 p.).

Response to Office Action Dated May 25, 2011; U.S. Appl. No. 11/762,295; Response Filed Aug. 17, 2011 (11 p.).

Final Office Action Dated Dec. 13, 2011; U.S. Appl. No. 11/762,295 (15 p.).

Response to Final Office Action Dated Dec. 13, 2011; U.S. Appl. No. 11/762,295; Response Filed Feb. 13, 2012 (13 p.).

Advisory Action Dated Feb. 22, 2012; U.S. Appl. No. 11/762,295 (4 p.).

RCE and Response to Final Office Action dated Dec. 13, 2011; U.S. Appl. No. 11/762,295; Response Dated Mar. 12, 2012 (17 p.).

European Search Report Dated Sep. 28, 2012; European Application No. 07798534.9 (5 p.).

* cited by examiner

METHOD AND APPARATUS FOR $CO_2$ SEQUESTRATION

CROSS-REFERENCE TO RELATED APPLICATIONS

This application is a continuation-in-part of U.S. patent application Ser. No. 11/762,295 filed Jun. 13, 2007 which claims benefit of U.S. provisional application Ser. No. 60/892,331 filed Mar. 1, 2007 and U.S. provisional application Ser. No. 60/804,763 filed Jun. 14, 2006, entitled "Method and Apparatus for $CO_2$ Sequestration", all hereby incorporated herein by reference. This application is also related to U.S. provisional application Ser. No. 61/056,628 filed May 28, 2008, hereby incorporated herein by reference.

STATEMENT REGARDING FEDERALLY SPONSORED RESEARCH OR DEVELOPMENT

Not applicable.

BACKGROUND

1. Field of the Invention

This invention relates generally to the field of $CO_2$ sequestration and more specifically to apparatus and methods for sequestering $CO_2$ using algae.

2. Background of the Invention

Increasing global levels of carbon dioxide ($CO_2$) has been a worldwide concern for some time. Measured in terms of volume, there were about 280 parts per million $CO_2$ in air at the beginning of the Industrial Revolution, and today there are 360 parts per million (ppm), a thirty percent increase. The annual increase is 2 ppm, and rising. If present trends continue, the concentration of $CO_2$ in the atmosphere will double to about 700 ppm in the latter half of the 21st century. Many scientists now believe that most of the global warming observed over the past 50 years can be attributed to this increase in carbon dioxide from human activities.

It is well known that green plants uptake $CO_2$ through photosynthesis. Photosynthesis converts the renewable energy of sunlight into energy that living creatures can use. In the presence of chlorophyll, plants use sunlight to convert $CO_2$ and water into carbohydrates that, directly or indirectly, supply almost all animal and human needs for food. Oxygen and some water are released as by-products of this process. The principal factors affecting the rate of photosynthesis are a favorable temperature, level of light intensity, and availability of carbon dioxide. Most green plants respond favorably to concentrations of $CO_2$ well above current atmospheric levels.

While there are a number of ways to increase carbon dioxide uptake in biological systems such as plants, it has proven difficult to do so cost effectively. Various strains of algae offer the fastest $CO_2$ uptake. Ocean based enrichment programs are invasive and may lead to more problems than they solve. Specifically they tend to grow weed and filamentous forms of algae and can damage or destroy entire ecosystems. Efficient methods of harvesting the algae produced by such means are not in advanced development.

Land-based algae systems are very effective in capturing $CO_2$, but are limited by available land space and cost. In an open passive or batch system, it is only possible to produce approximately 150 metric tons of dry biomass from algae per hectare per year. Using these figures, it would require over 200 hectares (495 acres) of open land to capture the output from a 1000-megawatt gas turbine power plant, not even taking into consideration weather and water availability.

Critical to the production of large amounts of algae is the presence of light. Algae use light to convert $CO_2$ into sugars, i.e. photosynthesis. Unfortunately, light only penetrates a few centimeters into an active culture of algae. As the algae organisms multiply and the culture density increases, the degree of light penetration decreases. Some researchers have used fiber optics as a light source but thus far this method has been prohibitively expensive and ineffective. Consequently, there is a need for apparatus and methods for sequestering $CO_2$ using algae, which exposes the algae to a sufficient amount of light in a cost-effective manner.

BRIEF SUMMARY

A method and apparatus for growing algae for sequestering carbon dioxide and then harvesting the algae includes a container for a suspension of algae in a liquid and a bioreactor having a translucent channel in fluid communication with the container to absorb $CO_2$ and grow the algae. A monitor determines the growth of the algae in the channel. A separator separates the grown algae from the suspension and an extractor extracts biomaterials from the grown algae.

The foregoing has outlined rather broadly the features and technical advantages of the present invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a detailed description of the preferred embodiments of the invention, reference will now be made to the accompanying drawings in which.

NOTATION AND NOMENCLATURE

Certain terms are used throughout the following description and the claims to refer to particular system components. This document does not intend to distinguish between components that differ in name but not function. In the following discussion and in the claims, the terms "including" and "comprising" are used in an open-ended fashion, and thus should be interpreted to mean "including, but not limited to . . . ".

DETAILED DESCRIPTION OF THE PREFERRED EMBODIMENTS

Figure 1:
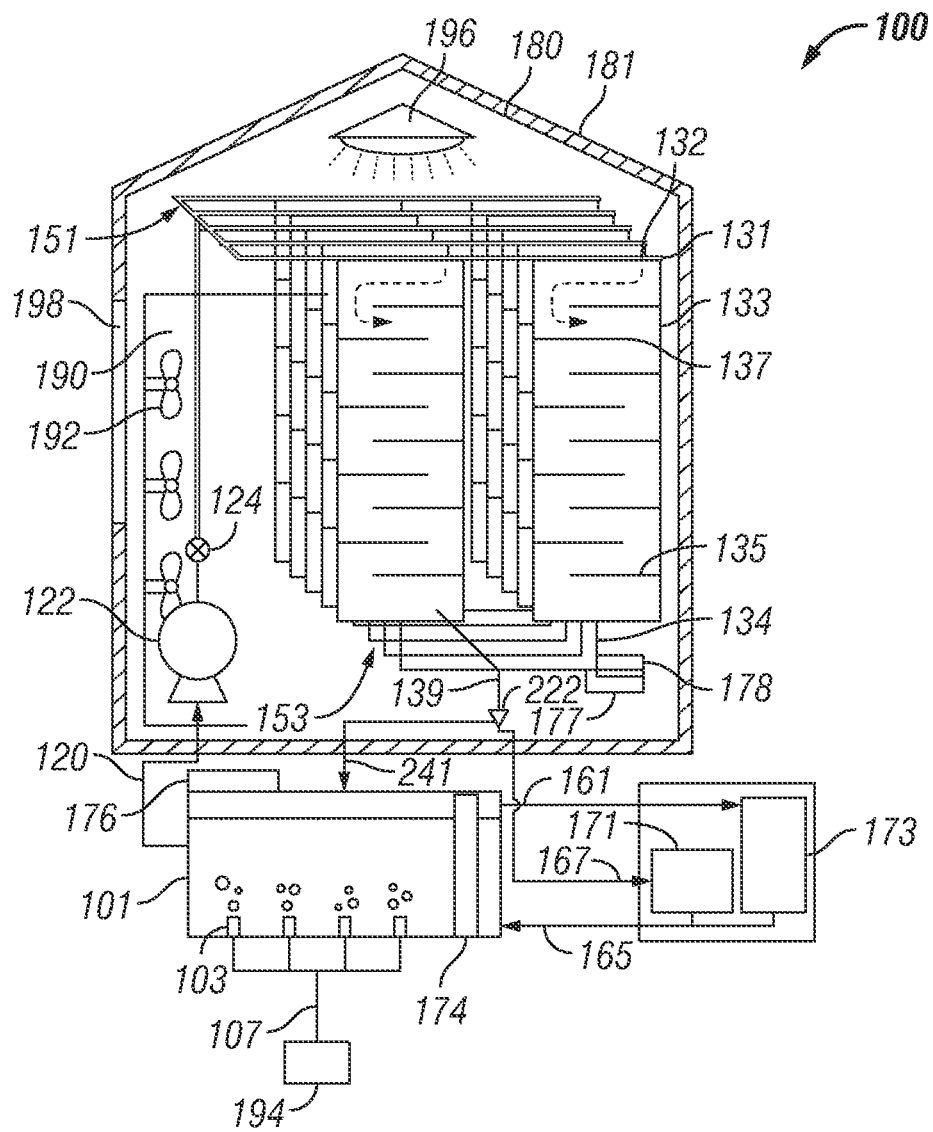
FIG. 1 illustrates a schematic of an apparatus for sequestering $CO_2$ using algae.

FIG. 1 illustrates an embodiment of a system for sequestering $CO_2$ using algae. In this embodiment, the system 10 includes an apparatus 100 with a culture tank 101, a pump 122, and one or more bioreactors 131. The culture tank 101, pump 122, and bioreactors 131 are in fluid communication with each other and are connected to each other via a plurality of conduits or lines.

The culture tank 101 is filled with a suspension of algae and water. In embodiments, the volume of the algae suspension is monitored by a volume meter 174 included in the culture tank 101. Typically, culture tank 101 has a rectangular structure. However, culture tank 101 may be of any configuration, i.e. cylindrical, known to one of ordinary skill that is optimal for culturing algae. Culture tank 101 is made of materials that are resistant to corrosion, such as polymers or stainless steel. In a preferred embodiment, culture tank 101 is constructed out of plastic, plastic liner, treated metal, or combinations thereof. Culture tank 101 also comprises at least one gas jet 103. According to another embodiment, culture tank 101 is closed to the atmosphere such that apparatus 100 is a closed system. Having a closed system prevents contamination of the algae suspension as well as evaporation of the water. Thus, the only gas entering culture tank 101 is through gas jets 103. Moreover, all culture medium and fluids entering bioreactors 131 are preferably sterile to prevent contamination. That is, the suspension is flowed through the bioreactors 131 under sterile conditions. As used herein, sterile conditions may refer to conditions known to those of ordinary skill in the art sufficient to maintain an aseptic environment free of contaminating germs or microorganisms.

The gas jets 103 introduce a $CO_2$-containing gas into culture tank 101. Gas jets 103 may comprise any type of suitable inlets such as valves, nozzles, gas diffusers or membranes. In a preferred embodiment, the plurality of gas jets 103 comprises a plurality of gas diffusers. Gas diffusers break up the introduced gas into smaller, more soluble bubbles. According to another preferred embodiment, a plurality of gas jets 103 is located at the bottom of culture tank. In an embodiment, gas jets 103 are provided a $CO_2$-containing gas from gas supply line 107 by a gas compressor 194. Gas compressor 194 pressurizes the gas for introduction to the algae suspension in the tank 101. Preferably, the gas is ambient air bubbled into the culture tank 101 where the $CO_2$ in the air is then dissolved in the algae suspension.

Generally, the algae suspension entering the feed conduit 120 has a predetermined $CO_2$ concentration. In an embodiment, the $CO_2$ level is no more than about 5,000 ppm, or alternatively preferably no more than about 2,500 ppm, or alternatively more preferably no more than about 1,000 ppm. $CO_2$ concentration beyond a certain level causes the algae suspension to become acidic, thereby stunting algae growth. The $CO_2$-enriched algae suspension is pumped from the culture tank 101 through feed conduit 120 to inlet manifold 151 for bioreactors 131. Feed conduit 120 extends from the culture tank 101 to the pump 122 and then from the pump 122 to the inlet manifold 151. Pump 122 is any suitable device capable of pumping the suspension. Examples of suitable devices include without limitation, centrifugal pumps, impeller pumps, or rotary pumps. In one embodiment, feed conduit 120 additionally comprises an air inlet valve 124 allowing more $CO_2$-containing gas to saturate the algae suspension. Air inlet valve 124 is a one-way valve that allows gas to enter the feed conduit 120, but does not allow any of the algae suspension to escape. Thus, the algae suspension is constantly being supplied with carbon dioxide.

Figure 7:
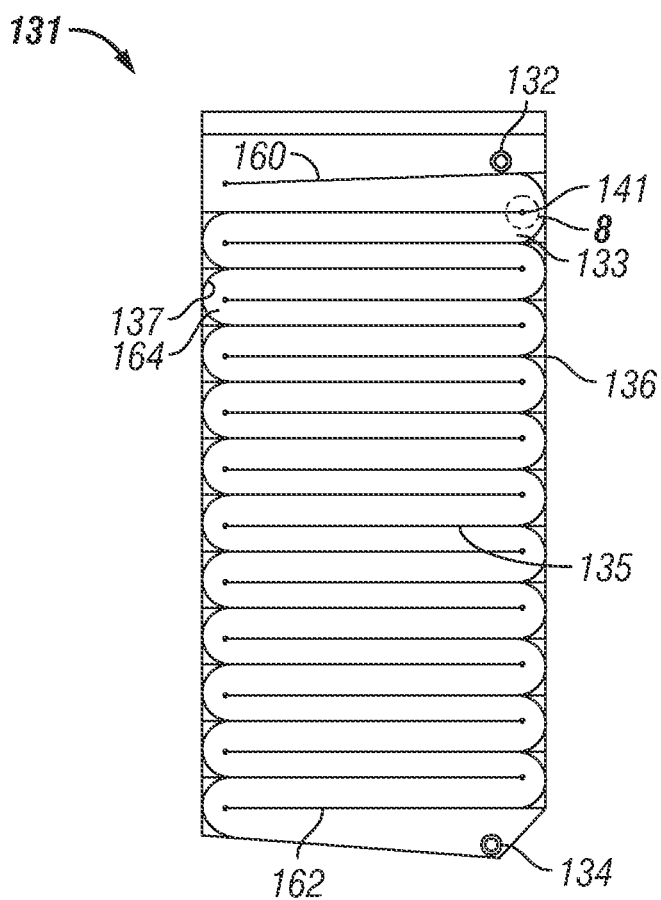
FIG. 7 is a front view of an alternative configuration of a bioreactor channel for a bioreactor.

Referring now to FIG. 2, inlet manifold 151 distributes the $CO_2$-enriched algae suspension to the inlets 132 of each bioreactor 131. The inlet 132 of each bioreactor 131 is preferably located on the top of each bioreactor 131 such that the algae suspension flows downward through the bioreactor 131 to the outlet 134. Generally, the outlet 134 is disposed on the same face and near the same edge of the bioreactor 131 as the inlet manifold 151 as illustrated in FIG. 7.

Referring again to FIG. 1, typically, outlets 134 are located at the bottom of each bioreactor and lead to an outlet manifold 153. The outlet manifold 153 may comprise a conduit made of a flexible hose material, such as but not limited to neoprene, silicon, rubber or other materials as known to one skilled in the art. Outlet manifold 153 distributes the flow into an outlet conduit 139. Outlet conduit 139 re-circulates the suspension with uncompleted growth algae back into culture tank 101 and/or separates the suspension with completed growth algae for extraction by separator 171.

In additional embodiments, outlet manifold 153 may have one or more vents 177 to purge any excess oxygen present in the bioreactors 131. The one or more vents may comprise one or more purge valves 178. Furthermore, the one or more vents may vent excess oxygen in a manner such as to maintain sterile conditions in the bioreactors 131.

Alternatively, each bioreactor 131 has an individual outlet conduit 139 coupled to each outlet 134. In another embodiment, each bioreactor 131 has an outlet conduit, which flows directly into culture tank 101. Further each bioreactor 131 may have an outlet conduit which directs the algae into the inlet of another bioreactor 131 before returning to the tank 101.

Referring to FIG. 1, an artificial light source 196 may be provided. Although the light source preferably is natural sunlight, one or more artificial light sources 196 may also be utilized. Examples of suitable artificial light sources are fluorescent lamps, halogen lamps, or other artificial lighting well known to one skilled in the art. In a specific embodiment, a combination of metal halogen lights and a sodium vapor lights is utilized. The artificial light sources may be arranged around the one or more bioreactors 131 to provide light to the algae within each bioreactor 131.

The one or more bioreactors 131 may be entirely covered by a protective shell 181 shown in FIG. 1. The function of the shell 181 is to prolong the life of bioreactors 131 and protect them from environmental elements such as wind, rain and direct sunlight. In an embodiment, the protective shell 181 is a Quonset-type shell. The Quonset-shell is preferably made of a weatherproof material that is permeable to light. Examples of suitable materials include without limitation, polyethylene, polycarbonate, polyvinylchloride, polypropylene, or glass. In a further embodiment, the protective shell 181 is a greenhouse-type enclosure. Furthermore, the protective shell may be directly affixed to the bioreactor rack 159 illustrated in FIGS. 9 through 12. In such embodiments, the heat produced within the greenhouse-type enclosure can be converted to electrical power for powering supplemental artificial light source 196.

Algae cultures preferentially grow and sequester $CO_2$ within specific temperature ranges. In embodiments, the optimal temperature ranges for $CO_2$ sequestering algae may be between about 10° C. and about 50° C., and more preferred between about 20° C. and about 30° C. It can be appreciated that this range is exemplary, as different species and strains of algae have different optimal growth temperatures. In embodiments, cooling or heating steps are taken when the temperature approaches within about 3° C. to about 5° C. of the end points of the optimal range. Furthermore, the regulation of shading, cooling and heating may change as a function of culture maturity. For example, after introduction to the bioreactor system 100, algae may be sensitive to increased light intensity and preferring shading while the algae acclimate. Light intensity, ambient temperature, and humidity are factors that have an affect on the culture temperatures. As a means to optimize $CO_2$ uptake, devices to control the amount of light, the temperature and the humidity surrounding the bioreactor 131 may be included in the protective shell 181. A removable shade 180, as shown in FIG. 1, may cover a portion, the top or all of a bioreactor 131 or shell 181. The shade 180 shields the bioreactor 131 and the algae suspension flowing therein from intense light. Additionally, the bioreactors 131 need to be kept within a temperature range favorable for $CO_2$ uptake by the algae. In order to address this property, a temperature control system 190 may be used. The system 190 may include liquid misters, fans, air conditioning units or combinations thereof for maintaining a favorable temperature. In preferred embodiments a system for controlling the temperature within the protective shell 181 may comprise fans 192 directing air across the exterior surface of the bioreactors 131. Additionally, the temperature control system 190 may include heaters 198, without limitation, in order to maintain algae suspension temperature in optimal ranges. Differential control of the shading, cooling and heating may be done manually or under the control of an automated system.

In a further embodiment, various lines such as inlet conduit 120 or outlet conduit 139 may be run underground to cool the culture medium and algae. The ground may act as a natural heat sink or heat exchanger to absorb heat from the warmer fluid within the lines, such as lines 120, 139. Even during the hot summer months, the ground may remain cool enough to cool the culture medium and algae flowing through apparatus 100. In another embodiment, culture tank 101 is located underground.

Figure 13:
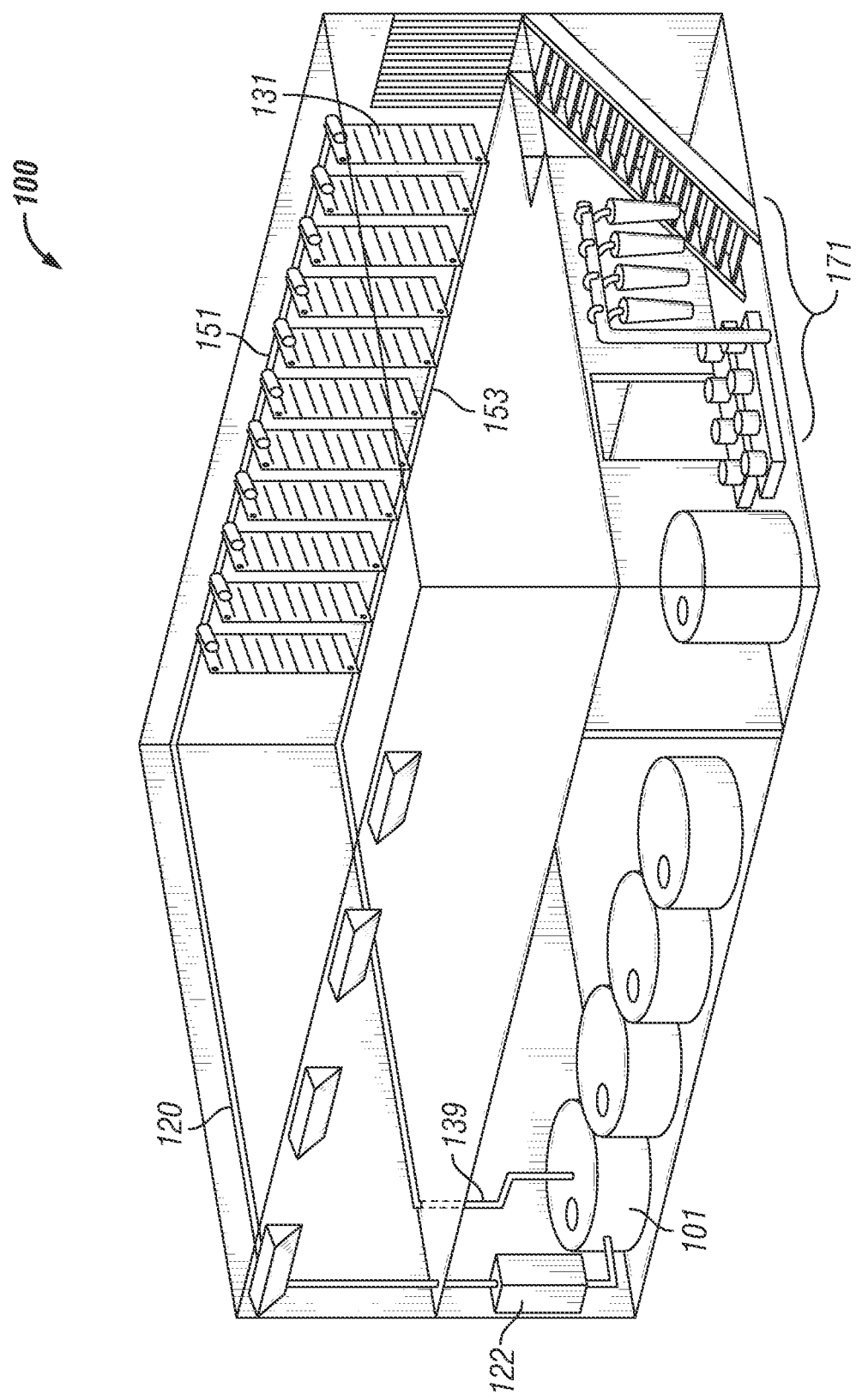
FIG. 13 is a perspective view, partly in cross-section, illustrating an embodiment of a two story $CO_2$ sequestration system.

As illustrated in FIG. 13, the apparatus 100 may be constructed as a two level building, such that the bioreactors 131 are positioned at a level above culture tank 101 and algae harvester 171. Thus, pump 122 pumps the algae suspension from underground culture tank 101 to the top of the bioreactors 131 through feed conduit 120. This arrangement facilitates access to the devices for cleaning, maintenance, repair and supplementing material into the algae suspension. Alternatively, culture tank 101 may be elevated at the same height as the top of bioreactors 131. In such embodiments, the algae suspension flows from culture tank into the inlet manifold 151 by gravity. Pump 122 can be envisioned to pump the algae suspension from outlet line 139 to culture tank 101.

Wherein the apparatus 100 comprises more than one bioreactor 131, algae may be circulated or cycled through each bioreactor 131 at least once to maximize exposure of the algae to light. Ultimately, the algae from the one or more bioreactors 131 eventually return to culture tank 101 and then are continuously re-circulated again and again through one or more bioreactors 131. Thus, the advantage of the continuous process is that even if some algae do not receive sufficient light in one cycle, chances are that those algae eventually will be exposed to light because of the continuous re-distribution of the algae through the one or more bioreactors 131.

Any suitable algae may be cultured in the tank 101. In a preferred embodiment, the algae species, *Chlorella*, is used. Other examples of suitable algae species include, without limitation, red algae, brown algae, *Spirulina*, or combinations thereof. According to preferred embodiments, the algae species is preferably non-filamentous so as not to clog the apparatus. In an embodiment, the algae species is a single-cell algae species ranging from about 1 micron to about 15 microns.

Generally, water, i.e. tap water or distilled water, is used to culture the algae. In an embodiment, the water is sterile and free from all contaminants. Alternatively, saltwater may be used to culture saltwater species of algae. However, any appropriate culture mediums known to those of skill in the art may be used depending on the specific algae species.

In other embodiments, a plurality of fish may be maintained in culture tank 101. The fish consume algae as well as produce nitrate in the form of feces. The fish feces are used to further nourish the algae. In further embodiments, culture tank 101 may include one or more feed inlets to introduce or provide additional nutrients to the algae. The one or more feed inlets may be coupled to one or more feed tanks filled with specific types of nutrients, minerals, mediums, or the like. In an embodiment, the one or more feed tanks may be disposed in series or in parallel to the culture tank 101. Preferably, feed inlets and feed tanks are maintained under sterile conditions.

The bioreactors 131 are generally constructed from any transparent or translucent polymeric material. In other words, a polymeric material that is permeable to light. Furthermore, the polymeric material is preferably a flexible material. A flexible material allows the bioreactor to compensate for different and varying flow rates as well as being easier to handle. In some cases, the polymeric material may even possess elastic properties. Furthermore, the polymeric material is UV treated to withstand repeated and extended exposure to light. In alternative embodiments, it can be envisioned that the polymeric material is a rigid material. Examples of suitable materials include without limitation, polypropylene, polystyrene, polypropylene-polyethylene copolymers, polyurethane, or combinations thereof. In a preferred embodiment, the bioreactors 131 are made of polyethylene. Any type of polyethylene may be used including high-density polyethylene or low-density polyethylene. A rigid material resists pressure, weight and flow velocity based deformations. Additionally, a rigid material may increase laminar flow of the algae suspension through the bioreactor 131.

The thickness of the polymeric material is in the range of about 3 mils (0.003 inches) to about 10 mils (0.010 inches), more preferably from about 4 mils (0.004 inches) to about 6 mils (0.006 inches). The polymeric material preferably has a tensile strength capable of withstanding the weight of the suspension flowing through the bioreactor, such as the weight of at least 50 gallons of suspension. The polymeric material is typically produced in the form of a tube and is heat sealable. The tubular polymeric material is folded forming adjacent sides that are heat sealed to close the upper and lower ends of the tubular polymeric material and to form internal flow channels 133, hereinafter described in further detail. It should be appreciated that the bioreactors 131 may be made from two planar sheets of polymeric material that are heat sealed along their periphery, sealing the sheets to form bioreactors 131. In embodiments, the bioreactors 131 may be made of a rigid material as previously described.

According to a preferred embodiment, bioreactors 131 are substantially planar in configuration. In an exemplary embodiment, each bioreactor is about 10 ft tall and about 2 ft wide, alternatively about 10 ft tall and about 4 ft wide, alternatively about 10 ft tall and about 10 ft wide. However, in other embodiments, each bioreactor may range from about 4 feet wide to about 30 feet wide and from about 5 feet tall to about 20 feet tall. Moreover, the height to width ratio of each bioreactor may be any ratio. In embodiments, the height to width ratio of each bioreactor may range from about 10:1 to about 1:1. In addition, each bioreactor 131 may have different heights and widths in order to optimize light exposure to the circulating algae.

Figures 2A, 2B:
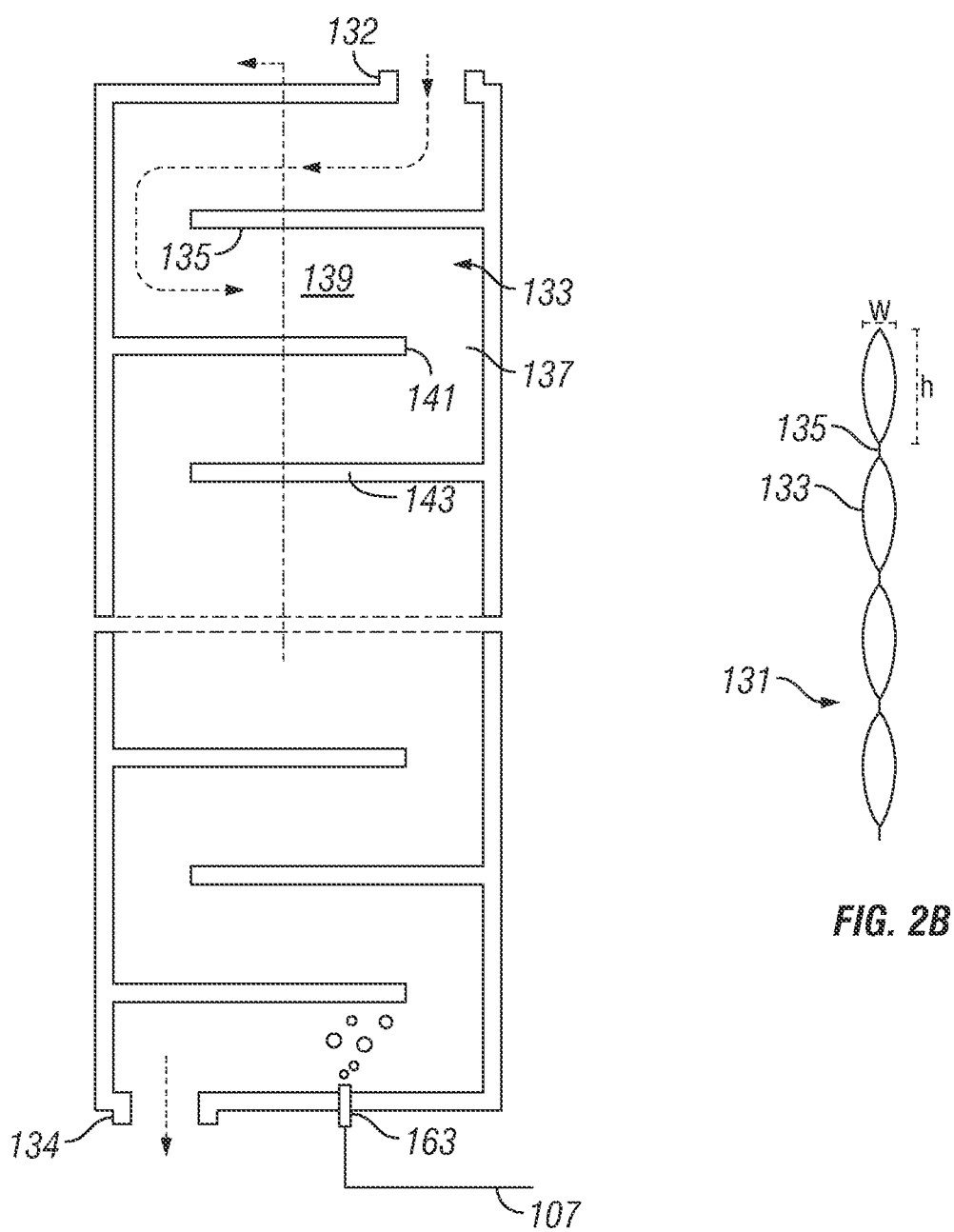
FIG. 2A illustrates a front view of an embodiment of a bioreactor culture channel.
FIG. 2B is a cross-sectional view of the baffles of the bioreactor shown in FIG. 2.

Referring to FIGS. 1, 2A and 2B, flow channels 133 are formed by a plurality of baffles or partitions 135. Baffles 135 serve to maximize the residence time of the algae in each flow channel 133. The greater the residence time of the algae, the longer the algae in the bio-reactor 131 is exposed to light. In embodiments, the residence time of the algae in bioreactors 131 may range from about 1 minute to about 60 minutes, alternatively preferred from about 5 minutes to about 45 minutes, alternatively more preferred from about 10 minutes to about 15 minutes. In an embodiment, the baffles 135 may be created by heat-sealing, ultrasonic welding or other methods for joining the polymeric material at specific locations along adjacent sides of the material.

Baffles 135 define the flow channel 133 within each bioreactor 131. FIG. 2B shows a cross-section of channels 133 in one embodiment of a bioreactor 131. In FIG. 2B, h refers to the height of each channel 133 (the space between each baffle 135) and w refers to the maximum width of each channel 133. Preferably, h is no more than about 3 inches. Additionally, in most embodiments, h is preferably no more than about 2 inches. The width, w, of each channel is set such that the algae flowing through each channel 133 receive sufficient light to survive and grow. The weight of the suspension flowing through the bioreactor stretches the non-rigid polymeric material causing the width w to be maintained at a minimum so as to allow the light passing through the polymeric material to reach all of the algae in the suspension flowing through the channels 133. This weight prevents the channels 133 from ballooning so as to increase the width w and prevent the light from reaching the algae flowing through the center of the channel 133.

In certain embodiments, baffles 135 are arranged in an alternating horizontal configuration to form generally horizontal channels 139 and return or end channels 137. Each horizontal channel 139 has an open end 141 and a closed end 143. End channel 137 is formed around the open end 141 of an upper baffle 135 together with a closed end 143 of an adjacent lower baffle 135. Baffles 135 form a serpentine configuration of the channel 133.

Channels 133 have configurations to minimize dead spaces in the channels. Dead spaces are fluid/air interfaces in the channels 133 where a pocket of air develops creating a dry pocket or area where there is no flow. These cause stagnant areas fostering contamination. The suspension tends to leave residue in the dead spaces such as polysaccharides forming secondary metabolites in the form of sugars and starches. This residue tends to stick to the walls of the channels 133 which then fosters the growth of bacteria that can harm the overall system. Therefore it is an objective to completely fill the channel and maintain fluid velocity as high as possible without buckling or pinching the walls of the bioreactor 131.

In embodiments it is preferred to create turbulent flow at potential dead spaces to prevent stagnant flow and contamination. Bioreactors 131 made of a material that can deform, distend or inflate allows the dimension of the channels 133 to vary thus making it difficult to ensure flow through potential dead spaces because the wall of the channel 133 is not longer smooth and uniform. In embodiments, a rigid bioreactor may be used such as a thermal formed plastic. With a rigid bioreactor, the flow through the bioreactor may be substantially laminar. It is desired that the suspension completely fill the channels 133 such that there are no dead spaces as the suspension flows through the bioreactor 131.

Figure 3:
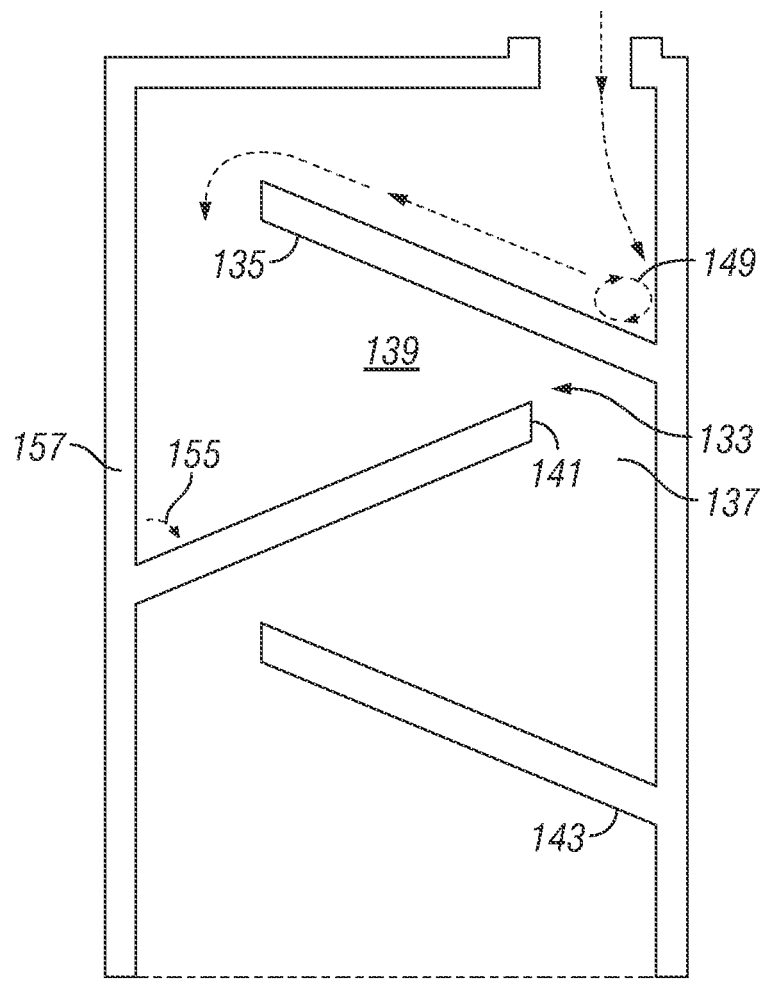
FIG. 3 is an enlarged view of another embodiment of baffles for a bioreactor culture channel.

Each baffle end 141, as shown in FIGS. 3 and 4, creates turbulence in the algae suspension as it flows downward through the bioreactor 131. The turbulence creates vortexes at these ends 141, which allow for better mixing of the algae suspension and prevention of dead spaces. As shown in FIG. 4A additional baffles may be configured in vertical orientations to the horizontally arranged baffles 135 to increase residence time of the culture suspension.

Referring now to FIG. 3, in an additional embodiment, baffles 135 may be angled upward to increase residence time of algae in bioreactor 131. That is, each baffle 135 forms an upward acute angle 155 with the side 157 of bioreactor 131 toward the top of bioreactor 131. A corner 149 or pocket is formed at the intersection of each baffle 135 and side 157 of bioreactor 131. Corner 149 may cause the formation of vortexes in the circulating algae and culture medium. As algae flows through bioreactor 131, the algae may circulate or swirl temporarily in the vortices or mixing zones formed at each corner 149 thus, altering laminar flow to turbulent flow and increasing exposure time of the algae in bioreactor 131 to light and preventing dead spaces. In some embodiments, baffles 135 may be angled downwardly as shown in FIG. 4D. Thus, it is envisioned that baffles 135 may be angled at any suitable angle from the side 157 of bioreactor 131 ranging from about 30° to about 160° from horizontal.

Figure 4A:
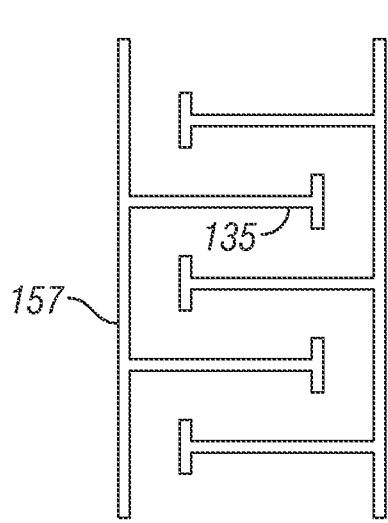
FIG. 4A is an elevation view of a bioreactor with vertical baffles.
Figure 4B:
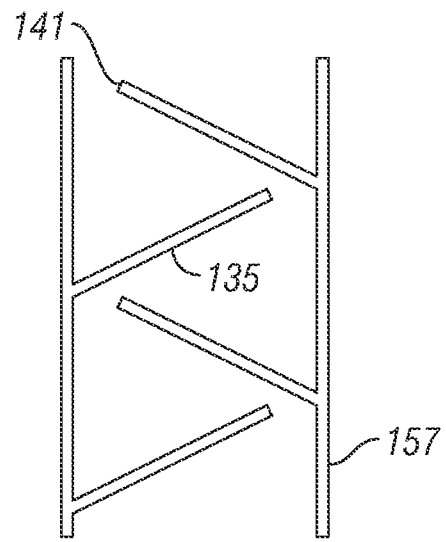
FIG. 4B is an elevation view of an embodiment having upwardly angled baffles.
Figure 4C:
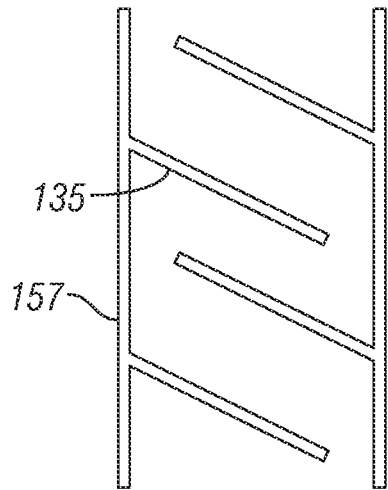
FIG. 4C is an elevation view of an embodiment having upwardly and downwardly angled baffles in a parallel configuration.
Figure 4D:
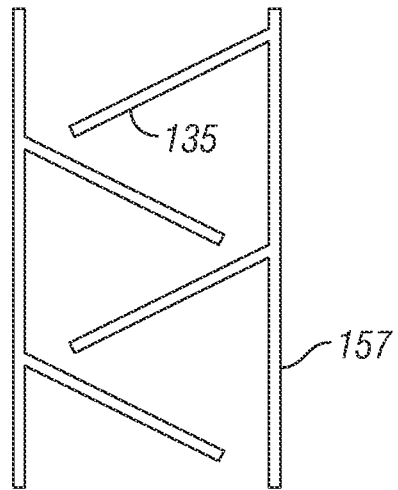
FIG. 4D is an elevation view of an embodiment having all downwardly angled baffles.

Referring now to FIGS. 4A-4D, in general, each baffle 135 is angled at the same angle. However, in other embodiments, each baffle 135 may be angled at different angles to each other. FIGS. 4A-D illustrate various configurations of baffles 135 which may be incorporated into bioreactor 131. FIG. 4B shows an embodiment where baffles 135 are all upwardly angled. FIG. 4C shows an embodiment where baffles 135 are configured in an alternating upward and downward angled parallel arrangement. FIG. 4D shows an embodiment where baffles 135 are all downwardly angled. It is to be understood that the arrangement of baffles 135 is not limited by these preferred embodiments, but may comprise an unlimited number of configurations to increase the sequestration of $CO_2$ by the algae. For example the baffles may be angled in the same direction, but retain different angles of elevation from horizontal. In embodiments with a plurality of bioreactors 131, each bioreactor may comprise a different baffle arrangement or configuration in order to optimize algae residence time.

Figure 5A:
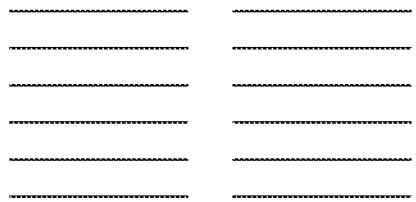
FIG. 5A illustrates a top view of a configuration of a plurality of bioreactors in a rectangular matrix formation.
Figure 5B:
FIG. 5B illustrates a top view of configuration of a plurality of bioreactors in another rectangular matrix configuration.
Figure 5C:
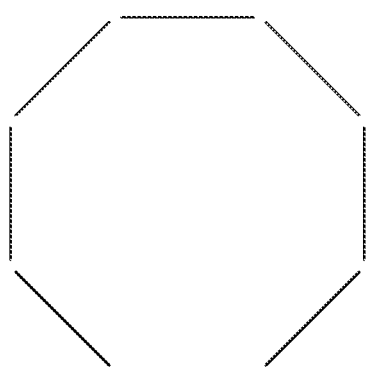
FIG. 5C illustrates a top view of a configuration of a plurality of bioreactors in a polygonal configuration.

Referring now to FIGS. 5A-5C, according to preferred embodiments, the plurality of transparent bioreactors 131 are suspended or hung vertically. Bioreactors 131 may be hung in any suitable configuration. However, it is desirable for bioreactors 131 to be hung such that each channel 133 is exposed to the maximum amount of light. FIGS. 5A-C depict a schematic top view of the different variations at which the bioreactors 131 may be hung or suspended from a top-down view. FIG. 5A shows a typical embodiment in which the bioreactors are configured in a rectangular matrix formation. For example, in FIG. 5A, the matrix is two bioreactors wide and 6 bioreactors deep. FIG. 5B shows yet another embodiment in which the matrix is 6 bioreactors wide and two bioreactors deep. In embodiments where bioreactors are arranged in a matrix formation, the bioreactors 131 preferably are no more than 6 inches apart. FIG. 5C illustrates another embodiment in which the bioreactors are arranged in a polygonal configuration. Thus, the bioreactors provide nearly unlimited possibilities in configurations so as to maximize exposure of the culture medium to light.

Figure 8:
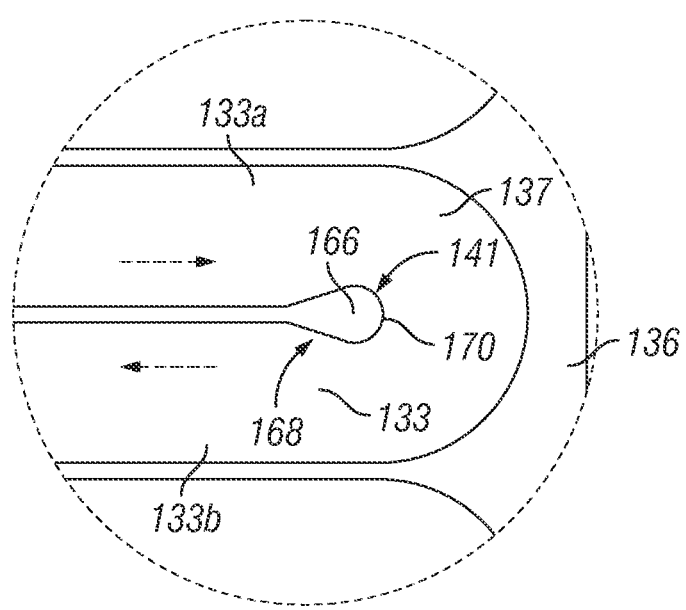
FIG. 8 is an enlarged view of Detail A shown in FIG. 7 illustrating an embodiment of the turn in a channel of the bioreactor baffle.

In further embodiments illustrated in FIGS. 7 and 8, the bioreactor 131 may have flow means in the channel 133 to improve suspension flow within the baffles 135. The flow means may include additional heat sealed areas 136 that prevent the suspension from becoming stagnant, immobile or settling. In exemplary embodiments, the bioreactors 131 include a sloped sealed area 160 in the baffle 135 immediately adjacent to the inlet 132, such that suspension does not become trapped between the inlet 132 and the outer edge of the bioreactor 131. Additionally, the bioreactor 131 includes a sloped bottom baffle 162 to maximize the flow of the algae suspension to the outlet 134. In certain embodiments, the end channels 137 are formed to create a curved or radiused channel 164 for the flow of the culture suspension. The radiused channel 164 may comprise a smaller cross-sectional area than channel 133. The smaller cross-sectional area acts to accelerate the flow through radiused channel 164 in a manner to induce additional turbulence in the following channel. Radiused channel 164 eliminates dead spaces, such as stagnant gas and fluid pockets, in bioreactor 131 that may permit contamination of algae suspension. Examples of contamination may include biofilms and degrading algae cells.

Referring to FIG. 8, the flow means formed by the baffle ends 141 may comprise alternative shapes such as but not limited to a triangle, a square, an ellipse, a circle or a teardrop such that the algae suspension flow increases turbulence about the baffle end 141. In most preferred embodiments a teardrop shaped baffle end 166 is oriented with the thin tapered end 168 facing into the flow on top channel 133a, while the blunted round end 170 faces the end channel 137. This orientation creates a gentle slope for flow of the suspension around and over the baffle end 141, before creating a sharper drop off into the end channel 137. Further, the shape of baffle end 141 creates turbulence by directing the flow through the channel 133 upward slightly before entering the channel end 137. The upward displacement of the liquid before cascading vertically through the channel end 137 to a lower channel 133b creates a vortex or turbulent swirl in the lower channel 133b without excessive flow interference. The teardrop shaped baffle end 166 reduces the cross-sectional area of the end channel 137 to accelerate flow from the larger top channel 133a into the smaller cross-sectional area of end channel 137. Fluid flow then passes into the larger cross-sectional area of lower channel 133b. The velocity of the flow over the teardrop shaped baffle 166 in the upper channel 133a creates a high pressure area due to Bernoulli's principle and/or a Venturi effect. As flow passes into the end channel 136, there is a pressure drop into the lower channel 133b causing turbulence and mixing. The turbulent flow of the algae suspension prevents the algae from clinging or sticking to the inside surfaces of the walls of the bioreactor 131. Furthermore, the baffle end 141 shapes may increase the durability of the bioreactor 131 by decreasing deformation, tearing, delaminating or other related plastic stress wear as understood by one skilled in the art.

In embodiments, the baffle end 141 is between about 0.25 inches and about 2 inches wide, preferably between about 0.25 inches and about 1 inch, and most preferably between about 0.5 inches and 0.75 inches wide. Other shapes of the baffle end 141 may alter flow through the channel so as to create vortices within the channel 133 prior to introduction to the channel end 137. The created turbulent swirl mixes the algae solution and gases within the bioreactor 131.

According to another embodiment, each bioreactor 131 includes a gas inlet 163 as seen in FIG. 2A. In an embodiment, a gas such as carbon dioxide is introduced (e.g. bubbled) in each bioreactor 131 through gas inlet 163. Gas inlet 163 is typically disposed at the bottom or lower end of each bioreactor 131. However, gas inlet 163 may be disposed at any portion of bioreactor 131. Furthermore, gas inlet 163 may include a valve for adjusting the flow of gas into bioreactor 131. The gas may be introduced from gas supply 107 or from another source such as ambient air. Any suitable gas may be introduced into bioreactor 131 through gas inlet. The gas introduced into bioreactor 131 may serve several purposes. For instance, the bubbling action of gas through the bioreactor 131 may facilitate further agitation and mixing of the algae and the culture medium within bioreactor 131. Without being limited by theory, the introduction of gas also may serve to maintain the rate of photosynthesis by the algae as the photosynthetic reaction is dependent on $CO_2$ concentration. If the $CO_2$ concentration within the bioreactor 131 drops too low, the algae may cease its photosynthesis. Moreover, introduction of $CO_2$-containing gas into bioreactor 131 via the gas inlet may provide a further means of absorbing or sequestering $CO_2$ from the ambient air.

Figure 9:
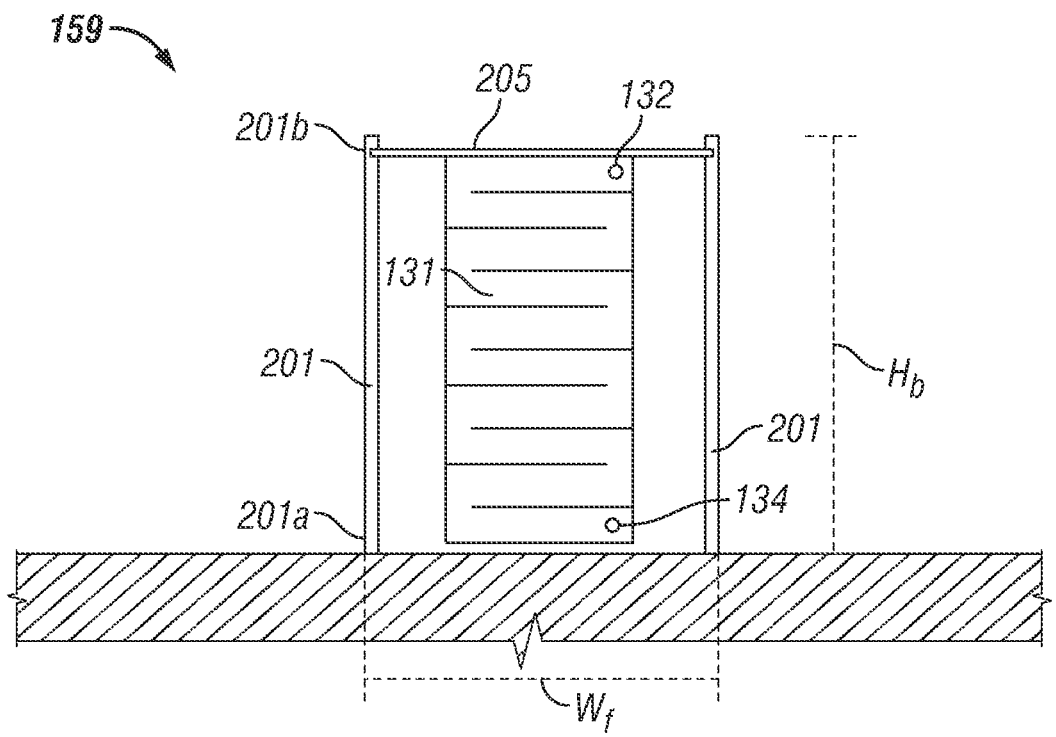
FIG. 9 is a front elevation view illustrating hanging racks for the bioreactor.
Figure 10:
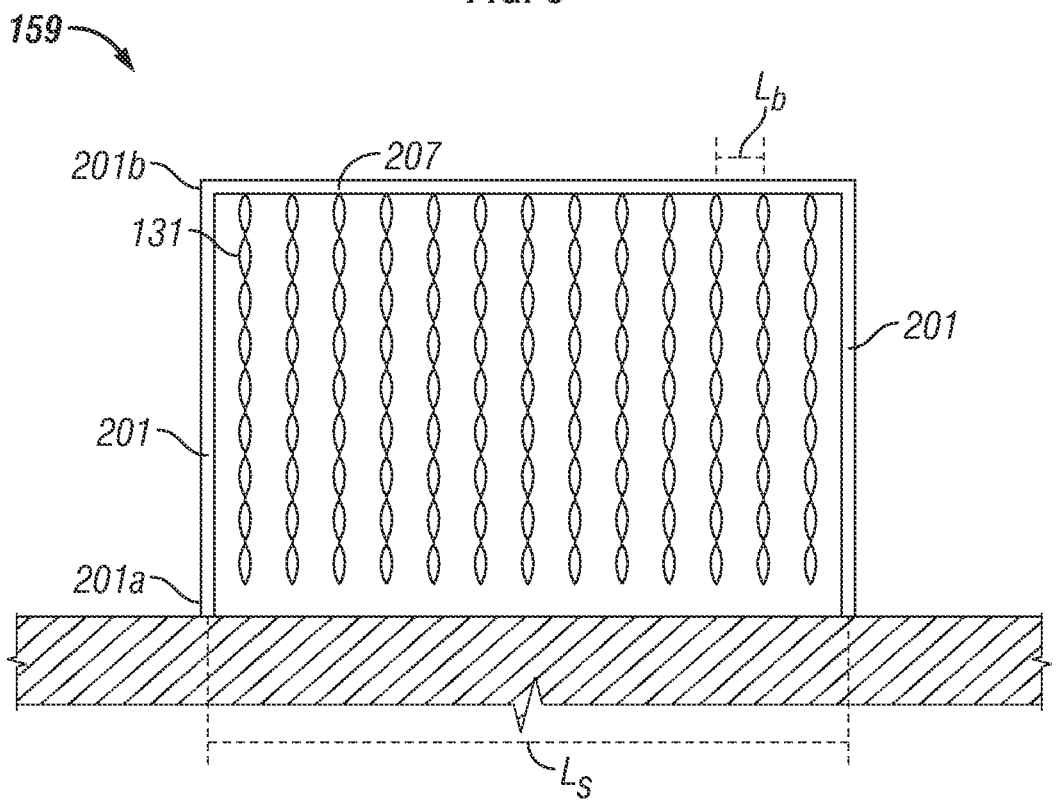
FIG. 10 illustrates a side elevation view of bioreactor hanging rack of FIG. 9.

Referring to FIGS. 9 and 10, in certain embodiments, bioreactors 131 are hung at different heights. In further embodiments, the reactors are hung from racks 159. The racks 159 may be comprised of about four parallel vertical support members 201 that are positioned approximately at the corners of a rectangle. Vertical support members 201 have a first lower end 201a located at ground level and a second upper end 201b vertically disposed from the first end 201a at a height $H_r$. The vertical support members 201 are positioned at a width $W_f$ apart in one dimension, such that $W_f$ is larger than the width w of the bioreactor 131. In another dimension, the vertical support members 201 are positioned at a length apart $L_s$. The vertically oriented support members 201 disposed thusly and connected by parallel beams 207, with a length of $L_s$, and a height above ground of $H_b$, at the second end 201b. The rack 159 for the support of at least one hanging member 205 is disposed between parallel beams 207 for hanging one or more bioreactors 131. The bioreactor hanging racks 159 are spaced a distance $L_b$ apart, such as no more than six inches. The height and width of the bioreactor hanging racks 159 is dependent on the dimensions of the bioreactors 131. In alternative embodiments, the hanging racks 159 may have alternate dimensions to hang bioreactors 131 at different heights, orientations and configurations. Hanging bioreactors 131 at different heights, orientations and configurations changes the flow rate of the algae suspension through each bioreactor 131. It is believed that differing flow rates for each bioreactor 131 provides improved distribution of light to each bioreactor 131

Figure 6:
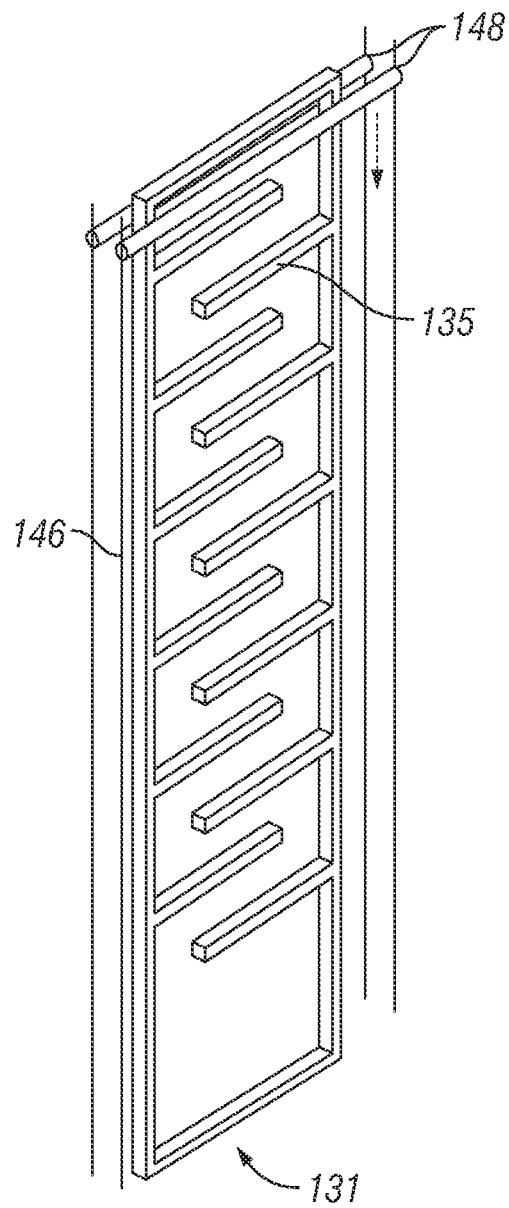
FIG. 6 is a perspective view of an apparatus for unsettling any settled algae in the channel of a bioreactor.

Referring now to FIG. 6, in an additional embodiment, bioreactor 131 may include an agitating means having at least two cleaning members 148 to cause any algae settling or clinging to the interior of the bioreactor 131 to drop off and flow through the bioreactor 131. In some embodiments, cleaning members 148 are elongate bars or rollers movably disposed horizontally on either face of bioreactor 131. In other words, bioreactor 131 is disposed in between agitation members. In an embodiment, agitation members 148 are coupled to vertical tracks 146 disposed on both sides of bioreactor 131. Agitation members 148 may compress bioreactor 131 between each member 148 and move vertically up or down the height of bioreactor 131 to unsettle any settled algae or to release any algae that has attached to the inner surface of bioreactor 131. Furthermore, agitation members 148 may be coupled to vertical tracks 146 by movable screw arms such that agitation members 148 move up and down to compress and release each bioreactor 131. Agitation members 148 may be operated by computer control or manually.

Figure 11:
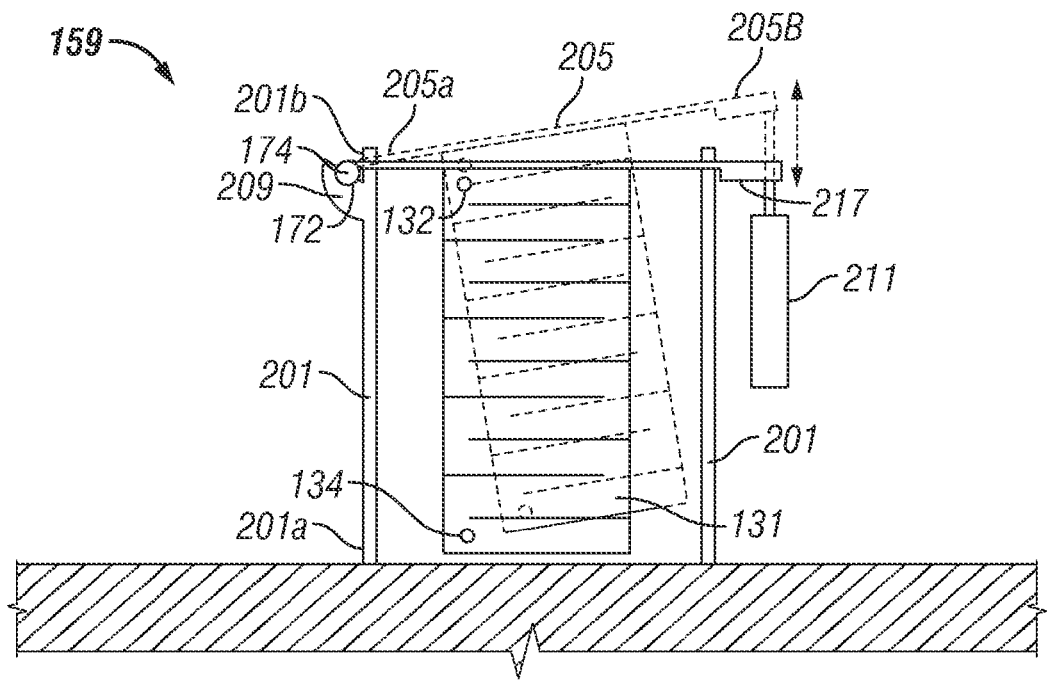
FIG. 11 illustrates a front elevation view of an actuator for hydraulically displacing a bioreactor hanging rack with bioreactor.
Figure 12:
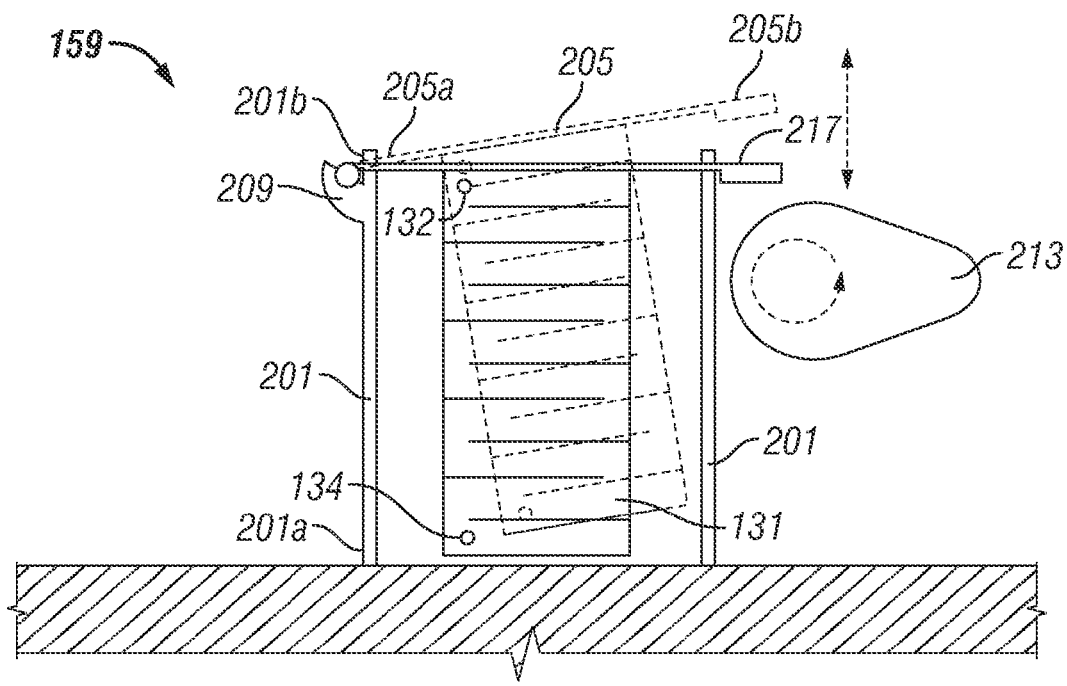
FIG. 12 illustrates a front elevation of an actuator for mechanically displacing a bioreactor hanging rack with bioreactor.

FIGS. 11 and 12 illustrate alternative agitation means to agitate algae suspension flow within the bioreactors 131 and can be manipulated to temporarily alter, agitate or displace the flow within the bioreactors 131. The agitation means may include an angling means for lifting one side of the bioreactor 131 and alter the angles of the channels 133 with respect to horizontal. The angling means may be any member that directionally displaces a bioreactor 131, such as but not limited to a piston, an actuator, a pushrod or a cam. In embodiments the hanging member 205 has a first end 205a and a second end 205b. A pivot connection 209 pivotably connects end 205a of the hanging member 205 to vertical support member 201. The pivot connection 209 can be any structure or device commonly known, such as a ball joint, a cradle or a hinge. As illustrated, cradle 172 may be disposed on vertical support 201, for receiving a pivot head 174 disposed on end 205a of member 205. The other end 205b of hanging member 205 is a free articulating end. The free end 205b having a first position, wherein the hanging member 205 remains substantially parallel with the ground, appreciably in contact with the rack 159, and a second position wherein the free end 205b is vertically displaced above the bioreactor 131, such as between about 2 inches and about 24 inches, preferably between about 2 inches and about 12 inches, and most preferably between about 4 inches and 6 inched above the first position. Disposed at the second end 205b may be a lifting member 217 to mechanically mediate the translocation of the free end 205b. The lifting member 217 is in mechanical interface with the lifting device 211 of FIG. 11 or cam 213 of FIG. 12. The lifting member 217 may be a part of the parallel bar 207, at the second end 205b of individual hanging members 205, at the ends of multiple hanging members or combinations thereof. The lifting member 217 can be envisioned as a pivot point, a ball joint or other mechanism to allow interaction or a linkage between the lifting member 217 and the lifting device 211.

In embodiments the action of the lifting device 211 or the cam 213 vertically disposes the free end 205b of the hanging member 205 for duration of time t. Time t maybe any suitable time to temporarily disrupt the flow of algae suspension through the bioreactor 131. In embodiments t is between about 2 minutes and about 60 minutes, preferably about 2 minutes and about 10 minutes, and more preferably between about 2 minutes and about 5 minutes. The lifting of one side of the bioreactor 131 as shown in broken lines in FIGS. 11 and 12, varies the flow rate and angle of the channel 133 and pools an additional volume of the algae suspension in the opposing channel ends 137. Upon lowering or replacing the raised end of the bioreactor 131, the volume of water released to flow varies across the channel 133. The rapid transfer of this volume across the channel 133 agitates, re-suspends and flushes sediment or settled algae from the channel 133. In alternative embodiments, the free end 205b may be lifted and lowered rapidly at least once to agitate, re-suspend and flush the channel 133. In preferred embodiments, the agitation means is activated periodically each day.

Figure 14:
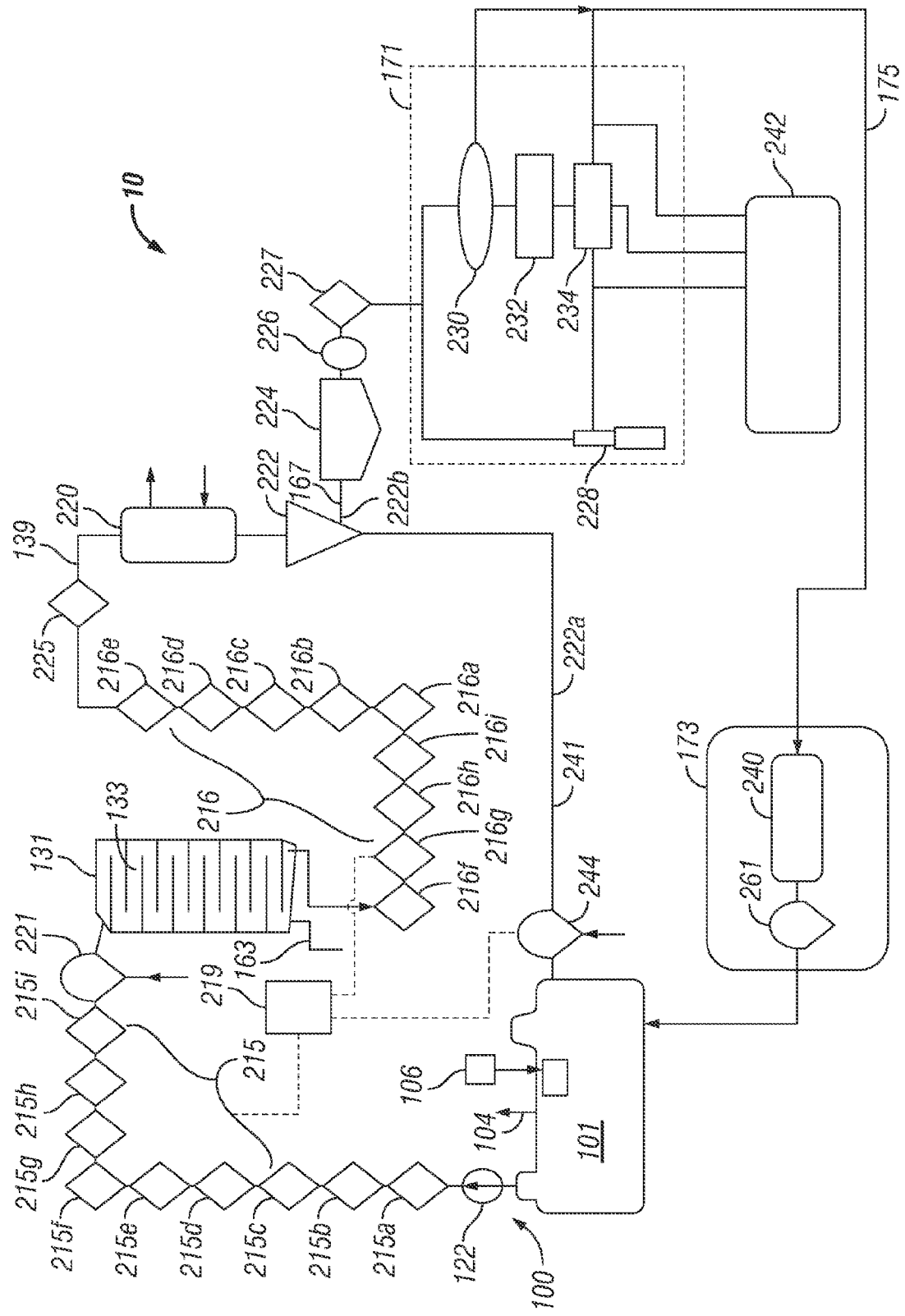
FIG. 14 is a process flow diagram of a $CO_2$ sequestrating system.

Referring to FIGS. 1 and 14, a plurality of sensors 215 monitor predetermined parameters of the algae suspension prior to introduction to the bioreactors 131. The algae suspension then flows down through the circuitous channels 133 of bioreactors 131 via gravity flow. As the suspension flows down through the bioreactors 131, the algae in the mixture are exposed to light, preferably natural sunlight. The algae uptakes or sequesters the $CO_2$ dissolved in the suspension and converts it into sugars and carbohydrates through the process of photosynthesis. In photosynthesis, a photon strikes a chloroplast within the organism. The chloroplast contains the compound chlorophyll. In the presence of chlorophyll and $CO_2$, a chemical reaction takes place forming carbohydrates, sugars, and oxygen. Thus, through the natural process of photosynthesis, the algae suspension sequesters the $CO_2$ and converts it into other useful carbon compounds. The produced compounds are a source of nutrients for the algae allowing further growth and production of algae. When no light is available, the algae go through cellular respiration, converting the sugars into energy for the production of further algae. In an embodiment, about 1,000 to about 1,200 tons of $CO_2$ per hectare (2.5 acres) of land may be sequestered a year.

After the algae suspension has flowed through bioreactor 131 the same predetermined parameters of the algae suspension are measured by sensors 216 disposed at the exit of the bioreactor 131. In embodiments, the sensors 215, 216 relay information about the algae suspension parameters to a computer 219 for comparison of the information against predetermined ranges. Computer 219 controls a nutrient pump 244 to inject nutrients to maintain the preferred and/or predetermined parameters for optimized algae growth.

Conditions of the suspension may be monitored using any suitable type monitoring devices. Variables that may be tracked using monitors 215 and 216 include without limitation, pH, temperature, conductivity, turbidity, dissolved oxygen, chlorophyll concentration, as well as the concentration of nitrates, ammonia and chloride. These variables may be recorded through out the process or apparatus 100.

In certain embodiments, the temperature of the algae suspension is monitored by temperature probes 215a and 216a, before and after the bioactors 131 respectively. As the suspension passes through bioreactor 131 as illustrated in FIG. 14, temperature is maintained between about 0° C. and about 50° C., preferably between 10° C. and about 40° C., and most preferably between about 15° C. and about 35° C. Regulation of the temperature of the culture is necessary to maximize the growth of the algae in bioreactors 131. High temperatures may kill the culture and low temperatures may impede growth or damage cells within the culture.

Dissolved oxygen concentration in algae suspension by monitors 215b and 216b is monitored to ensure the algae are continuing photosynthesis. Photosynthesis requires $CO_2$ and high concentrations of dissolved oxygen inhibits this process.

The dissolved oxygen concentration is in a range of about 0 mg/L to about 50 mg/L, preferably about 0 mg/L to about 30 mg/L and most preferably between about 6 mg/L and about 8 mg/L. $CO_2$ and other gases may be bubbled into the algae suspension to decrease the dissolved oxygen concentration.

The turbidity of the solution is tracked by monitors 215c and 216c to maintain the suspension within a range of about 0 NTU to about 300 NTU, preferably between about 20 NTU and about 200 NTU and most preferably between about 150 NTU and about 200 NTU. Turbidity is a further measure of solids, particulate and microscopic matter suspended in a liquid. In the apparatus 100, the turbidity data aids in determining cell density.

The flow rate of the algae suspension is dependent on the height of bioreactors 131 and other factors. The flow rate is tracked by monitors 215d and 216d. In general, the flow rate of the suspension flowing through each bioreactor may range from about 1 gallon/hr to about 100 gallons/hr, preferably from about 5 gallons/hr to about 75 gallons/hr, more preferably from about 10 gallons/hr to about 50 gallons/hr. Alternatively, the flow rate of the algae suspension through the bioreactors may range from about 1 cm/s to about 50 cm/s, preferably from about 3 cm/s to about 25 cm/s, more preferably from about 5 cm to about 15 cm/s.

Chlorophyll is the green pigment found in algae. The chlorophyll concentration is monitored by monitors 215e and 216e before and after flowing through bioreactors 131. Chlorophyll concentration is maintained to be within the range of about 0.01 mg/L to about 8 mg/L. The concentration of chlorophyll in the algae suspension is one factor in determining the maturity of the algae in the suspension. Additionally, the concentration of the chlorophyll in the bioreactors 131 influences the light penetration into the media and the quantity of light reaching the interior of the bioreactor 131.

The conductivity of the algae solution is an indicator of the quantity and types of nutrients and minerals in the suspension. Monitoring the conductivity within predetermined parameters at monitors 215f and 216f verifies the total dissolved solids within the suspension before and after the suspension flows through bioreactor 131. The conductivity is maintained within the range of about 50 µS/cm to about 30,000 µS/cm, preferably between about 500 µS/cm and about 3,000 µS/cm and most preferable between about 500 µS/cm and about 1,500 µS/cm.

Nitrogen is a nutrient for the successful culturing of algae as it is a key component in the biosynthetic pathways to produce chlorophyll and proteins within the algae. In order to maintain an actively growing algae culture within the bioreactor 131, a level of accessible nitrogen compounds, or nitrates, is maintained in the suspension. It is preferred to maintain a nitrate concentration between about 0 mg/L and about 200 mg/L in the suspension. Monitors 215g before and 216g after the suspension passes through bioreactor 131 notify computer 219 if the nitrate concentration varies from the predetermined range. Ammonia may be an additional nitrogen source that is monitored in suspension and has monitors 215i and 216i. In embodiments, the ammonia concentration in the water is regulated to maintain a range of about 0 mg/l to about 50 mg/L.

In exemplary embodiments, the pH is maintained in a range of about 0.5 to about 13.5 dependent on the species of algae. In order to identify fluctuations in pH, it is monitored by monitors 215h and 216h before and after the bioreactors 131. The pH is preferred between about 5.5 and about 8, and most preferably between 6.5 and 8. Acidic or basic environments are unfavorable to grow concentrations of algae. If the pH of the media changes, it may identify changes within the algae culture, or inhibit the growth of the culture. Additional gaseous $CO_2$ may be bubbled into algae suspension prior to introduction to bioreactor 131 by $CO_2$ jet 221 or by jet 163 to adjust the pH of the solution.

Ion chloride is beneficial to regulate the osmotic balance within the suspension of algae. The chloride content of the media is dependent on the natural environment of the algae; fresh water species require a lower salinity concentration. In embodiments, the range of chloride concentration is maintained at between about 0 mg/L and about 100 mg/L. Monitors may be included to monitor the ion chloride.

The algae suspension leaving the bioreactors 131 may pass through an algae growth monitor 225. Algae growth or concentration in suspension may be monitored by measuring the light level, which penetrates each bioreactor 131. For example, if the light level is less than about 250 foot-candles, algae growth has likely reached a saturation point or density in which light cannot penetrate the innermost areas of bioreactors. In another embodiment, algae growth or concentration may be measured using methods or devices known by those skilled in the art to measure cell density (i.e. cells/mL of culture solution). For example, devices and methods such as without limitation, a Coulter Counter® Micro-sizer 3 or centrifugation may be used to determine cell density. Upon reaching a predetermined cell growth or density, the algae may be harvested as hereinafter described.

The algae may now be directed to a collector tank 220. The collector tank 220 collects the algae suspension from multiple bioreactors 131. In certain embodiments, the collector tank 220 may include a means to introduce gases to the suspension, or alternatively to vent gases from the suspension. The collector tank 220 may be in fluid communication with a separator 222. The separator 222 divides the algae suspension into separate process streams.

The separator 222 routes the algae suspension into the separate streams based on the measured parameters of the algae growth monitor 225. FIG. 14 illustrates the separator 222 that divides the algae suspension into two parts an uncompleted growth algae part 222a, and/or a completed growth algae part 222b.

In one embodiment, the uncompleted growth algae part 222a of the algae suspension stream is returned to the algae tank 101 by conduit 241. The algae suspension may have nutrients, algae cells or other biomaterials without limitation added to the suspension by an injection means 244 in conduit 241 before return to the algae tank 101. The tank 101 includes an oxygen vent 104 and a compressed air inlet 105 receiving compressed air from a compressor 106.

Once it is determined that algae growth has reached a predetermined cell density or other parameter, the suspension with completed growth algae is separated by separator 222 and is routed to a settler 224 by conduit 167. The completed growth algae part 222b of the algae suspension is then pumped through harvest conduit 167 to an algae harvester 171.

Settler 224 initiates the process of harvesting by routing algae suspension to the harvester 171. The settler 224 filters the algae from the suspension. Once the suspension ceases flowing and agitation, the algae will settle out of the liquid suspension. The liquid media may then be decanted or skimmed from the settled algae and recycled back into the algae tank 101. Removal of excess media from the algae suspension by the settler 224 creates a high viscosity slurry of algae.

Alternatively, the algae may be kept in the settler 224 for a predetermined time period to starve the algae. In embodiments, starving the algae may act to stimulate, stress, or otherwise initiate the production of desirable biomaterials within the algae. Biomaterials may include, without limitation, proteins, carbohydrates, oils, fats, nucleic acids, or other biological materials known to one skilled in the art. Additionally, other chemicals may be added to the settler to increase production of the desired biomaterials. The algae slurry is pumped from the settler 224 by slurry pump 226 to harvesting system 171. The rate at which the slurry is pumped to the harvesting system may be monitored by a monitor 227 at the pump 226.

Generally, the algae harvester 171 is used to remove and recover algae so that it can be used for other purposes. In embodiments illustrated in FIGS. 1 and 14, conduit 167 runs from the separator 222 to algae harvester 171. In alternative embodiments, the bioreactor outlet conduit 139 may run directly from the bioreactor 131 to the algae harvester 171. Generally, algae harvester 171 comprises a filter, skimmer, centrifuge or other means to strain out algae from the algae suspension.

In embodiments, the algae may be isolated from the media suspension by centrifuging. The centrifuge 230 creates a paste, pellet or bolus of algae, with the media floating on top. Removal of the liquid media leaving an algae paste. In further embodiments, the remaining media may further be removed from the paste by spray drying the algae. From a spray dryer 232 the algae goes to a biomaterial extractor 234.

In another embodiment, algae is filtered from the algae suspension and then deposited on a conveyer belt. The conveyor belt passes through a drying chamber or a heater to dry the algae. The dried algae are then collected for future use. In some embodiments, the dried algae are used to produce oil. The filtered water is returned to culture tank 101 through a recycle conduit 165 shown in FIG. 1.

In general, the disclosed methods and apparatus are capable of reducing the $CO_2$ level in an area by an amount ranging from about 100 ppm to about 1,900 ppm.

An algae extraction process is described in U.S. Patent Application No. 61/056,628, filed May 28, 2008, entitled Method and Apparatus for Algae Separation, hereby incorporated herein by reference. The algae separation apparatus 228 includes a micro-bubble flocculation column with an inlet and outlet, a micro-bubble generator, and an electrical charge generator. The micro-bubble generator generates micro-bubbles, preferably having a size less than 100 μm, with the electrical charge generator placing a charge on the micro-bubbles that is opposite to the charge of the algae. The algae enter through the inlet and are mixed with the charged micro-bubbles by the cavitations of the liquid in the column to form a froth. The resultant froth is comprised primarily of air. The micro-bubbles are sized to float the algae of a certain size, shape, and/density vertically up through the micro-bubble flocculation column. At a point where the algae reach its highest point in the column, the outlet in the column removes the algae and froth. In exemplary embodiments, the froth carries the algae within a certain size range to the outlet for isolation from the media. The algae are then withdrawn as a slurry at the outlet for extraction of the desired biomaterials from the algae. A negative pressure may be applied at the outlet to assist the removal of the algae from the column.

The algae slurry is than transported to extractor 234 where it is processed to extract certain biomaterials. Extraction may be conducted by any means known to one skilled in the art. In embodiments, the extraction method may be super critical fluid extraction, solvent extraction, or cold press expeller extraction, in preferred embodiments the extraction technique is super critical fluid extraction. Once the biomaterials are extracted, they may be transported to a separation system 242. In embodiments oils are separated for processing independently from other biomaterials such as proteins, sugars or other biomaterial, without limitation.

The water and media suspension that is removed from harvester 171 is transported by return conduit 175 to a water reclamation device or recycler 173. The water recycler 173 includes means to treat algae growth media. The media may require sterilization to remove any contaminating micro-organisms prior to return to tank 101. Sterilization may be conducted by any means as known to one skilled in the art, including but not limited to boiling, steam, pressure or irradiation. The media and water are moved through a UV sterilizer 240 to kill any contaminant organisms. Additional nutrients, media and water may be added to the suspension to make up for the loss in the harvesting system by nutrient pump 264.

Additionally, illustrated in FIG. 1, water vapor is pumped from culture tank 101 to water recycler 173 via the water recycle conduit 161. In certain embodiments, the water recycler 173 includes a condenser, which condenses the water vapor. Furthermore, the water recycler 173 comprises a filtration system to purify the water and a make-up water/nutrients supply 261 before sending the recycled water back to the culture tank 101. Alternatively, water recycler 173 may comprise any device known to those of skill in the art used to purify water.

Although the present invention and its advantages have been described in detail, it should be understood that various changes, substitutions and alterations may be made herein without departing from the scope of the invention as defined by the appended claims. Likewise, the sequential recitation of steps in the claims is not intended to require that the steps be performed sequentially, or that a particular step be completed before commencement of another step.

What is claimed is:

1. A system for removing $CO_2$ from air using algae, the system comprising: a culture tank for a suspension of algae in a liquid; a bioreactor in fluid communication with the culture tank to absorb $CO_2$ and grow the algae, the bioreactor having a plurality of translucent, substantially horizontal channels therethrough in an alternating horizontal arrangement from top to bottom of the bioreactor and vertical end channels connecting adjacent substantially horizontal channels to form a continuous flow path for the suspension from the top of the bioreactor to the bottom of the bioreactor, the enclosed horizontal channels and end channels being made from a flexible polymeric material and the bioreactor being adapted to be hung vertically for gravity flow of the suspension through the continuous flow path; a monitor determining the growth of the algae in the channels and adjusting a parameter of the suspension of algae to maintain a predetermined range of the parameter; a separator to separate grown algae; and an extractor to extract biomaterials from the grown algae.

2. The system of claim 1 further including a pre-monitor to determine a parameter of the algae from the group consisting of pH, temperature, conductivity, turbidity, dissolved oxygen, chlorophyll concentration, nitrate concentration, ammonia concentration, and Chloride concentration, prior to the algae entering the bioreactor or after leaving the bioreactor.

3. The system of claim 1 wherein a temperature sensor is disposed at the end of the bioreactor to measure a temperature of the suspension whereby the temperature is maintained between 0° C. and 50° C.

4. The system of claim 1 wherein a gas bubbler bubbles gases into the suspension entering the top of the bioreactor to maintain a dissolved oxygen concentration in the range of about 0 mg/L to about 50 mg/L.

5. The system of claim 1 wherein the monitor determines the turbidity of the suspension to maintain a turbidity of the suspension in the range of 0 NTU to about 300 NTU.

6. The system of claim 1 wherein the monitor determines flow rate to maintain the suspension at a flow rate through the channel from about 1 gallon per hour to about 100 gallons per hour, the channels varying in size depending upon the flow rate of the suspension.

7. The system of claim 1 wherein the monitor determines the concentration of chlorophyll to maintain a chlorophyll concentration in the suspension in the range of 0.01 mg/L to about 8 mg/L.

8. The system of claim 1 wherein the monitor determines conductivity to maintain a conductivity of the algae in the range of 50 µS/cm to about 30,000 µS/cm.

9. The system of claim 1 wherein the monitor monitors ammonia to maintain nitrogen in the algae between about 0 mg/L to about 200 mg/L.

10. The system of claim 1 wherein the monitor monitors the suspension to maintain a pH in the range of about 0.5 to about 13.5, $CO_2$, being introduced into the suspension by a jet to adjust the pH.

11. The system of claim 1 wherein the monitor monitors chloride to maintain a chloride concentration of the suspension between 0 mg/L and about 100 mg/L.

12. The system of claim 1 further including a device for measuring density to determine the cell density of the algae.

13. The system of claim 1 further including a conduit providing flow communication from the bioreactors to the culture tank, the culture tank includes a gas jet to introduce gas into the culture tank for culturing the algae.

14. The system of claim 13 wherein the conduit includes a nutrient pump to add nutrients to the suspension.

15. The system of claim 1 further including a compressed air source providing compressed air to the culture tank.

16. The system of claim 1 further including a settler to separate the algae from the liquid in the suspension while algae is flowing through the bioreactor.

17. The system of claim 2 further including an algae harvester to harvest the algae and an algae oil separator.

18. The system of claim 1 further including a pump with flow monitor to pump the algae suspension to the extractor.

19. The system of claim 1 wherein the extractor includes a centrifuge receiving the algae suspension to further remove liquid from the algae suspension and a dryer to dry the algae.

20. The system of claim 1 wherein the extractor removes biomaterials from the algae.

21. The system of claim 1 wherein the extractor includes a separation system for removing biomaterials from of the algae.

22. The system of claim 21 wherein the biomaterials include oils.

23. The system of claim 1 further including a conduit from the extractor transporting liquid to the culture tank.

24. The system of claim 23 wherein the conduit is configured to flow through a sterilizer, and is in fluid communication with a nutrient pump configured to make-up for any nutrients lost.

25. An apparatus for sequestrating $CO_2$ comprising: a translucent bioreactor having a generally planar configuration, hanging vertically and having a single downwardly extending flow path therethrough for the continuous gravity flow of a suspension containing algae in the presence of light from an inlet at a top of the bio-reactor to an outlet at a bottom of the bioreactor; and the single flow path including a channel including a plurality of adjacent generally horizontal linear portions connected by a generally vertical connecting portion, the generally vertical connecting portion having a cross-section smaller than a cross-section of the plurality of generally horizontal linear portions, the plurality of generally horizontal linear portions being in an alternating arrangement from top to bottom of the bioreactor.

26. The apparatus of claim 25 wherein a first threshold is formed between an end of the first generally horizontal linear portion with an increasing taper and a second threshold is formed between the generally vertical connecting portion and a second generally horizontal linear portion with a decreasing taper.

27. The apparatus of claim 26 wherein the generally vertical connecting portion is radiused.

28. The apparatus of claim 25 wherein the channel is made of a rigid, translucent material that is continuously exposed to light.

29. An apparatus for growing algae, comprising: a plurality of bioreactors, each vertically disposed on a support and each having a top and a bottom, the bioreactors each having a plurality of translucent, substantially horizontal channels connected together by vertical end channels to form a continuous flow path from the top to the bottom of the bioreactor for flowing an algae suspension therethrough; the support extending across the top of the bioreactor; an agitation means configured to agitate the bioreactor to alter the flow of the algae suspension as it flows through the channels; and a harvester to remove the algae from the algae suspension.

30. The apparatus of claim 29 the agitation means includes an angling member that directionally displaces at least one of the bioreactors to disrupt the flow of the suspension through the channels of the at least one bioreactor.

31. The apparatus of claim 30 wherein the angling member causes one end of he at least one bioreactor to pivot upwardly.

32. The apparatus of claim 29 wherein the bioreactors are housed in a temperature regulated enclosure.

33. The apparatus of claim 29 wherein the agitation means comprises a member having a pivot connection to raise and lower one end of the support.

34. The apparatus of claim 29 wherein the external agitator comprises at least one member configured to compress the cross-section of channels of the bioreactor.

35. The apparatus of claim 29 wherein the algae is removed from the suspension by centrifugation.

36. The apparatus of claim 29 wherein the algae is removed from the suspension by micro-bubble flocculation.

37. The apparatus of claim 29 wherein the bioreactor comprises a flexible polymeric channel.

38. The apparatus of claim 29 wherein the channel includes tapers and radiuses to prevent algae suspension stagnation.

* * * * *